United States Patent
Malawer et al.

[11] Patent Number: 5,597,551
[45] Date of Patent: Jan. 28, 1997

[54] LOW VOC HAIR SPRAY COMPOSITION

[75] Inventors: Edward G. Malawer; Kolazi S. Narayanan, both of Wayne, N.J.; James P. Cullen, Bartonsville, Pa.; Colleen M. Rocafort, Lake Hiawatha, N.J.

[73] Assignee: ISP Investments Inc., Wilmington, Del.

[21] Appl. No.: 369,016

[22] Filed: Jan. 5, 1995

[51] Int. Cl.$^6$ .............................. A61K 7/11; A61K 9/107
[52] U.S. Cl. ..................... 424/47; 424/78.02; 424/70.11; 424/DIG. 1; 424/DIG. 2; 514/957; 514/937
[58] Field of Search ................................ 424/47, DIG. 1, 424/DIG. 2, 78.02, 70.11, 70.19, 70.21, 70.22, 70.27; 514/957, 937

[56] References Cited

U.S. PATENT DOCUMENTS

| | | | |
|---|---|---|---|
| 4,897,262 | 1/1990 | Nandagiri et al. | 424/70.11 |
| 5,021,238 | 6/1991 | Martino et al. | 424/DIG. 1 |
| 5,158,762 | 10/1992 | Pierce | 424/47 |
| 5,176,898 | 1/1993 | Goldberg et al. | 424/47 |

OTHER PUBLICATIONS

Martino, G. T., et al. (1992). Spray Technology & Marketing, Mar. Issue, pp. 34–39.
Johnsen, M. A. (1992). Spray Technology & Marketing, Jun. Issue, pp. 32–40.

*Primary Examiner*—Raj Bawa
*Attorney, Agent, or Firm*—Walter Katz; Marilyn J. Maue; Joshua J. Ward

[57] ABSTRACT

A low volatile organic compound hair spray composition in the form of a stable, clear, single phase microemulsion in which the particles therein have a diameter of less than 1 micron, consisting essentially of by weight, (a) a butyl half-ester of a copolymer of maleic anhydride and ethyl vinyl ether in an amount of about 2–10%, optionally neutralized up to 20 mole %, (b) poly(methyl vinyl ether) as a surface active polymer in an amount of at least 0.75 to 1 part of (a);

(c) a secondary surfactant that is a polyethoxylated glyceryl fatty acid ester in an amount of at least 0.1%, and which has a hydrophilic-hydrophobic balance of greater than 10, (d) ethanol in an amount of 20 to 50%, and (e) water to 100%.

8 Claims, No Drawings

LOW VOC HAIR SPRAY COMPOSITION

BACKGROUND OF THE INVENTION

1. Field of the Invention

This invention relates to hair spray compositions, and, more particularly, to low VOC hair spray compositions of a water-insoluble polymer in the form of a stable, clear, single phase system wherein substantially all particles therein have a diameter of less than 1 micron, i.e. a microemulsion.

2. Description of the Prior Art

Hair spray compositions generally are solutions of a hair fixative polymer and a solvent, usually ethanol, water or ethanol-water mixtures, such as described in U.S. Pat. Nos. 4,543,249; 4,923,694; 5,266,308; 5,085,859; 5,173,290; 5,176,898; and PCT WO 93/03705. Such compositions also may contain small quantities of one or more adjuvants normally found in cosmetic products including a small quantity of a surfactant. The presence of a surfactant in a hair spray composition reduces the surface tension between the aqueous and polymer phases in the composition, and provides sprays having a desirable small droplet size or mist. U.S. Pat. Nos. 4,543,249 and 5,176,898, for example, describe such a surfactant-containing system for water-soluble fixative polymers. Similarly, U.S. Pat. No. 5,085,859 discloses a hair treating composition containing a film-forming material which is an interpenetrating polymer network of a substituted vinyl copolymer having a polar functionality and a non-polar silsesquioxane. This patent suggests that the interpenetrating polymer might be incorporated into the composition as an emulsion or microemulsion; however, such formulations are not disclosed for an interpenetrating polymer, or for any other polymer.

Water-insoluble polymers, such as the ethyl and butyl half-esters of copolymers of maleic anhydride and methyl vinyl ether, known as GANTREZ®-ES resins, and sold by International Specialty Products (Wayne, N.J.), have been used for many years as the hair fixative resin of choice in alcohol-based hair spray compositions, both in non-aerosol (pump) and aerosol (propellant) delivery systems. Recent California state legislation, however, has required that future commercial hair spray compositions contain a low volatile organic compound (VOC) content therein, particularly 80% or less VOC (by 1994) and 55% or less VOC (by 1998). In order to meet the strict VOC standards, it has been necessary for hair spray formulators to substantially reduce the alcohol content and to substantially increase the water content of existing hair spray products. However, for water-insoluble polymers, such as GANTREZ®-ES resins, which do not dissolve readily in water-based systems, such changes produce two-phase systems, which is undesirable from a commercial standpoint.

Accordingly, it is an object of the present invention to provide a low VOC hair spray composition containing a water-insoluble polymer in the form of a clear, single phase system.

Another object of the invention is to provide a 55% or less VOC hair spray composition in the form of a clear, single phase system which includes a water-insoluble polymer, a surfactant and a solvent, and in which substantially all the particles therein have a diameter of less than 1 micron.

Still another object of the present invention is the provision of a stable, clear, single phase, water-based, 55% or less VOC, pumpable or propellant-actuated hair spray composition including the ethyl half-ester of a copolymer of maleic anhydride and butyl vinyl ether as the water-insoluble hair fixative, poly(methylvinyl ether) as a surface active polymer, a secondary surfactant, alcohol and water.

A particular object of the invention is to provide a stable, clear, single phase hair spray composition of a water-insoluble hair fixative resin in the form of a microemulsion.

Still another object herein is to provide a hair spray concentrate of a water-insoluble hair fixative polymer in the form of a clear, viscous system and which, upon dilution with water and alcohol, will form a clear, single phase, low VOC hair spray composition in which substantially all the particles therein have a diameter of less than 1 micron.

These and other objects and features of the invention will be made apparent from the following more particular description of the invention.

SUMMARY OF THE INVENTION

A low VOC, preferably 55% or less, hair spray composition is provided herein which is a stable, clear, single phase system of a water-insoluble polymer in which substantially all the particles therein have a diameter of less than 1 micron, i.e. a microemulsion, preferably 0.1 micron or less, and optimally 0.05 micron or less, which comprises, by weight:

(a) a water-insoluble polymer, preferably the ethyl half-ester of a copolymer of maleic anhydride and butyl vinyl ether, optionally neutralized up to 20 mole %, preferably 5–15 mole %, and optimally 8–12 mole %, in an amount of less than 30%, preferably 2–10%, and optimally 4–6%;

(b) poly(methyl vinyl ether) as a surface active polymer, in an amount of at least 0.75 to 100 parts of (a), suitably at least 0.75 to 1 part of the water-insoluble polymer, if (a) is unneutralized, and at 10 mole % neutralization of (a), suitably 0.02 to 1 part of (a), preferably 0.8–1.2 parts, and optimally 1:1;

(c) a secondary surfactant, preferably a polyethoxylated glycol ether of glyceryl isostearate or monoleate, in an amount of at least 0.1%, preferably 0.2–2%, and optimally 0.5–1.5%;

(d) alcohol, preferably ethyl alcohol, in an amount of 55% or less, preferably 30–50%, and optimally 35–45%; and (e) water to 100%, preferably 38–67.8%, and optimally 47.5–60.5%.

Such low VOC hair spray compositions may be made by solvent dilution of a hair spray concentrate in the form of a clear, viscous liquid, comprising, by weight:

(a) a water-insoluble polymer in the amount of less than 55%, preferably 20–45%, and optimally 30–40%, (b) poly(methyl vinyl ether) as a surface active polymer in the amount of at least 18%, preferably 20–40% and optimally 21–34%;

(c) a secondary surfactant in the amount of at least 0.5%, preferably 1.4–18%, and optimally 3–12%; and (d) alcohol to 100%, preferably 34–73.6%, and optimally 48–67%.

A water-insoluble polymer is solubilized with and without neutralization in an alcohol-water mixture in about 50:50 wt. ratio with poly(methyl vinyl ether) as a surface active polymer in a weight ratio of 100 parts of the water-insoluble polymer to at least 0.75 part of the surface active polymer.

Neutralized water-insoluble polymers are solubilized in an alcohol/water mixture containing >40% alcohol.

The low VOC hair spray compositions of the invention may be applied by a pump or propellant spray delivery system, preferably a pump system, as a fine spray having a good spray pattern. The fixative film thus-formed on the hair of the user exhibits the desirable performance characteristics of excellent long-term hold and high humidity curl retention, good stiffness, and combability.

DETAILED DESCRIPTION OF THE INVENTION

In the present invention, solubilization of a water-insoluble polymer, such as the ethyl half-ester of a copolymer of maleic anhydride and butyl vinyl ether, into a low VOC, water-based, alcoholic hair spray composition which is a stable, clear single-phase system having a particle size of less than 1 micron in diameter, i.e. a microemulsion, is accomplished in the system herein by predetermining (1) the kind and amount of water-insoluble resin, (2) the kind and amount of a surface active polymer, (3) the extent of neutralization of the water-insoluble polymer, as described below, (4) the kind and amount of secondary surfactant, and (5) the ratio of alcohol-to-water.

(1) WATER-INSOLUBLE POLYMER

Suitable water-insoluble polymers for use herein include alkyl half-esters of copolymers of maleic anhydride and an alkyl vinyl ether. Such polymers have the general formula:

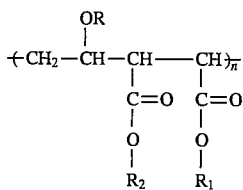

where $R=C_1-C_{18}$ alkyl, preferably methyl, $R_1=R_2=H$ or $C_1-C_{18}$ alkyl, preferably butyl, at least one of $R_1$ or $R_2=H$, and $n=50-1000$, preferably 100.

One such polymer is GANTREZ® ES-425, (International Specialty Products), which is commercially available as a 50% solution of the resin in ethanol. The commercial solution may be used directly to prepare the hair spray composition of the invention.

Suitably, the water-insoluble resin is present in an amount of up to 20% by weight of the composition, preferably 2–10%, and, optimally 4–6%.

(2) NEUTRALIZATION OF WATER-INSOLUBLE POLYMER

The water-insoluble polymer may be neutralized, if desired, to an extent of up to 20 mole % of the polymer, preferably 5–15 mole %, and, optimally 8–12 mole %.

Suitable neutralizing agents include aminomethylpropanol (AMP), dimethylstearylamine (DMSA), tertiary-isopropanolamine (TIPA), didodecylamine (DDA) and triethanolamine (TEA).

(3) SURFACE ACTIVE POLYMER

Poly(methyl vinyl ether) is the surface active polymer for use in the hair spray composition of the invention. This polymer is sold as GANTREZ® M (International Specialty Products) as a 50% solution in water.

The surface active polymer is present in an amount of at least 0.75 to 1 part of the weight of unneutralized water-insoluble polymer, preferably 0.8–1.2, and, optimally at 1:1 wt. ratio. For neutralized resin, the amount of surface active polymer is reduced, at 10 mole % neutralization, for example, it is about 0.02 to 9 part of water-insoluble polymer.

(4) SECONDARY SURFACTANT

Suitable secondary surfactants for use herein include ethoxylated glyceryl fatty acid esters, suitably with an HLB of >10, preferably about 12–18, and optimally about 14–16, and containing about 5–50 ethylene oxide (EO) units, preferably 15–35, and optimally about 20–30.

The alkyl group of the fatty acid ester suitably includes about 10–18 carbon atoms, saturated or unsaturated, e.g. stearyl, isostearyl, oleyl, etc. Tagat® I (PEG-30 glyceryl isostearate) (Goldschmidt) or Tagat® 02 (polyoxyethylene glycerol monoleate) surfactant compounds are preferred. Other suitable surfactants include ethoxylated natural wool fat, e.g. Ethoxylan® 1686 (PEG 75 lanolin); and a quaternized lanolin such as Lanoquat® 1751A.

Mixtures of surfactants also may be used herein. Accordingly the compound cocoamidopropyl betaine (Velvetex® Blc 35) may be used as a cosurfactant.

The secondary surfactant is present in an amount of at least 0.1%, preferably 0.2–2%, and, optimally 0.5–1.5%, by weight of the composition.

(5) ALCOHOL

Ethanol is present in the composition in an amount of 55% or less, preferably 30–50%, and, optimally 35–45%, corresponding to a VOC of 55% or less.

(6) WATER

Water is present to 100% of the composition, preferably 38–67.8%, and, optimally 47.5–60.5%.

The hair spray compositions of the invention exhibit those physical characteristics indicative of a microemulsion, that is, a stable, clear, single phase system in which substantially all the particles therein have a diameter of less than 1 micron, preferably less than 0.1 micron, and, optimally less than 0.05 micron.

The hair spray composition of the invention may be made by solvent dilution from a hair spray concentrate which is a stable, clear, viscous liquid, comprising, by weight:

(a) the water-insoluble polymer as a solid in the amount of less than 55%, preferably 25–45%, and optimally 30–40%;

(b) the surface active polymer in an amount of at least 18%, preferably 20–40%, and optimally 21–34%, (c) the secondary surfactant in the amount of at least 0.5%, preferably 1.4–18%, and optimally 3–12%;

(d) alcohol in an amount of 15–55%, and preferably 20–55%, and (e) water to 100%.

The low VOC hair spray compositions of the invention may be applied by a pump or propellant spray delivery system, preferably a pump system, as a fine spray having a good spray pattern. The fixative film thus-formed on the hair of the user exhibits the desirable performance characteristics of excellent long-term hold and high humidity curl retention, good stiffness, and combability.

Working examples of the invention and their performance during use are given in Table 1 below. The results were obtained using a Seaquist Euromist II pump spray system capable of delivering a 140–160 µl output from an actuator of 0.018"×0.010" deep. The pH of the compositions was 4.89–4.97.

TABLE 1

| Comp. No. | Water-Insoluble Polymer (as solid) | Wt. Water-Insoluble Polymer (as solid) | Neutralizing Agent | Wt. Neutralizing Agent | Surface Active Polymer | Wt. of Surface Active Polymer | Secondary Surfactant | Wt. of Secondary Surfactant | Wt. Ethanol | Wt. Water | Appearance of Composition |
|---|---|---|---|---|---|---|---|---|---|---|---|
| 1 | ES-425 | 4.9 | AMP | 0.2 | P(MVE)* | 0.1 | Tagat I | 1.25 | 44.7 | 48.9 | Clear, soluble |
| 2 | ES(225/425) | 3.5/ 0.1–1.0 | AMP | 0.2 | P(MVE) | 0.1 | Tagat I | 1.25 | 44.7 | 48.9 | Clear, soluble |
| 3 | ES-425 | 20 | AMP | 0 | P(MVE) | 20 | Tagat I | 1.30 | 29.35 | 29.35 | Clear, soluble |
| 4 | ES-425 | 20 | AMP | 0 | P(MVE) | 20 | Tagat I | 0 | 30.0 | 3.0 | Slightly cloudy, Some particulates |
| 5 | ES-425 | 20 | AMP | 0 | P(MVE) | 0 | Tagat I | 1.30 | 39.35 | 39.35 | Cloudy, 2 Layers |
| 6 | ES-425 | 20 | AMP | 0 | P(MVE) | 0 | Tagat I | 0 | 40.0 | 40.0 | Cloudy, 2 Layers |
| 7 | ES-425 | 5 | AMP | 0 | P(MVE) | 5.0 | Tagat I | 1.30 | 44.35 | 44.35 | Clear, soluble |
| 8 | ES-425 | 5 | AMP | 0 | P(MVE) | 5.0 | Tagat I | 0 | 45.0 | 45.0 | Cloudy emulsion |
| 9 | ES-425 | 5 | AMP | 0 | P(MVE) | 0 | Tagat I | 1.3 | 46.85 | 46.85 | Cloudy, 2 layers |
| 10 | ES-425 | 5 | AMP | 0 | P(MVE) | 0 | Tagat I | 0 | 47.5 | 47.5 | Cloudy, 2 layers |
| 11 | ES-425 | 20 | AMP | 0.46 | P(MVE) | 0 | Tagat I | 0 | 39.76 | 39.78 | Clear, some insoluble particles |
| 12 | ES-225 ES-425 | 4.67 0.09 | TIPA | 0.4 | P(MVE) | 0.08 | Tagat I | 1.06 | 42.93 | 50.77 | Clear |
| 13 | ES-225 ES-425 | 4.29 0.47 | TIPA | 0.4 | P(MVE) | 0.08 | Tagat I | 1.06 | 38.23 | 50.77 | Clear |
| 14 | ES-225 ES-425 | 4.41 1.10 | TIPA | 0.46 | P(MVE) | 0.1 | Tagat I | 1.23 | 49.67 | 43.04 | Clear |
| 15 | ES-425 | 4.89 | AMP | 0.22 | P(MVE) | 0.1 | Tagat 1 | 1.25 | 44.9 | 48.64 | Clear |
| 16 | ES-425 | 4.50 | AMP | 0.22 | P(MVE) | 0.5 | Tagat I | 1.25 | 44.9 | 48.64 | Clear |

*P(MVE) - Poly(methylvinyl ether)

Table 2 below provides a suitable hair spray concentrate for making the end-use hair spray compositions of the invention upon dilution of the concentrate with a predetermined mixture of ethanol and water.

TABLE 2

| | Concentrate |
|---|---|
| Ingredient | C-1 |
| Gantrez ® ES-425 (as solid) | 25 |
| Neutralizing agent, (AMP/TIPA) | 0 |
| Gantrez ® M | 20.0 |
| Tagat I | 1.5 |
| Ethanol | 26.0 |
| Water | 27.5 |
| Total | 100.0 |

For example, hair spray compositions were made from the concentrate of Table 2 in the following manner:

TABLE 3

| Ingredient | To Obtain HSC-1 | To Obtain HSC-2 |
|---|---|---|
| Concentrate | 20 | 20 |
| AMP | 0 | 0.2 |
| Ethanol | 40 | 39.8 |
| Water | 40 | 40.0 |
| Total | 100.0 | 100.0 |

The final hair spray compositions were:

TABLE 4

| Ingredient | HSC-1 | HSC-2 |
|---|---|---|
| ES-425 | 5.0 | 5.0 |
| AMP | — | 0.2 |
| Gantrez M | 4.0 | 4.0 |
| Tagat I | 0.3 | 0.3 |
| Ethanol | 45.2 | 45.0 |
| Water | 45.5 | 45.5 |
| Total | 100.0 | 100.0 |

Table 5 below shows the advantageous performance of the hair spray composition of the invention during use under standard test conditions. The results are shown for hair spray compositions HSC-1 and HSC-2 in Table 5.

TABLE 5

Performance of Hair Spray Compositions of Invention

| | Composition No. | |
|---|---|---|
| Characteristic | HSC-1 | HSC-2 |
| Film clarity | Clear | Clear |
| Film hardness | 5H | 4H |
| Long term hold - 90 min (%) | 90 | 88 |
| Dry time (sec.) | <200 | <200 |
| Duration of tack (sec.) | <60 | <60 |
| Stiffness | 7–8 | 7–8 |
| Non-flaking | Yes | Yes |
| Combability | 9.0 | 7.0 |
| Removability | Acceptable | Acceptable |
| Pump spray droplet particle size (μ) | 100–150 | 100–150 |

TABLE 5-continued

Performance of Hair Spray Compositions of Invention

| Characteristic | Composition No. | |
| --- | --- | --- |
| | HSC-1 | HSC-2 |
| Pump spray pattern (in.) | 3–3½ | 3–3½ |
| Pump spray pattern | Fine | Fine |

While the invention has been described with particular reference to certain embodiments thereof, it will be understood that changes and modifications may be made which are within the skill of the art. Accordingly, it is intended to be bound only by the following claims, in which:

What is claimed is:

1. A low volatile organic compound hair spray composition in the form of a stable, clear, single phase microemulsion in which the particles therein have a diameter of less than 1 micron, consisting essentially of by weight,
   (a) a butyl half-ester of a copolymer of maleic anhydride and ethyl vinyl ether in an amount of about 2–10%, optionally neutralized up to 20 mole %,
   (b) poly(methyl vinyl ether) as a surface active polymer in an amount of at least 0.75 to 1 part of (a);
   (c) a secondary surfactant that is a polyethoxylated glyceryl fatty acid ester in an amount of at least 0.1%, and which has a hydrophilic-hydrophobic balance of greater than 10,
   (d) ethanol in an amount of 20 to 50%, and
   (e) water to 100%.

2. A low VOC hair spray composition according to claim 1 wherein
   (a) is 2–10%,
   (b) is 1.5–20%,
   (c) is 0.2–2%,
   (d) is 20–50%, and
   (e) is 20–50%.

3. A low VOC hair spray composition according to claim 1 wherein
   (a) is 4–6%
   (b) is 1.5–6%,
   (c) is 0.5–1.5%,
   (d) is 40–50%, and
   (e) is 42–60%.

4. A low VOC hair spray composition according to claim 1 wherein the particle size is 0.1 micron or less.

5. A low VOC hair Spray composition according to claim 1 wherein its spray particle size is 0.05 microns or less.

6. A hair spray composition according to claim 1 wherein (c) has an hydrophilic-hydrophobic balance of 12–18.

7. A hair spray composition according to claim 1 wherein (c) has 5–50 ethylene oxide units.

8. A hair spray composition according to claim 1 wherein (c) is the polyethylene glycol ether of glyceryl isostearate or polyoxyethylene glycerol monoleate.

* * * * *